United States Patent
Hayashi

(10) Patent No.: US 10,352,869 B2
(45) Date of Patent: Jul. 16, 2019

(54) INSPECTION APPARATUS

(71) Applicant: Yazaki Corporation, Tokyo (JP)

(72) Inventor: Ryuhei Hayashi, Shizuoka (JP)

(73) Assignee: YAZAKI CORPORATION, Minato-ku (JP)

( * ) Notice: Subject to any disclaimer, the term of this patent is extended or adjusted under 35 U.S.C. 154(b) by 22 days.

(21) Appl. No.: 15/725,634

(22) Filed: Oct. 5, 2017

(65) Prior Publication Data

US 2018/0106728 A1   Apr. 19, 2018

(30) Foreign Application Priority Data

Oct. 14, 2016   (JP) ................. 2016-202444

(51) Int. Cl.
| | | |
|---|---|---|
| *G01N 21/88* | (2006.01) | |
| *G06T 7/00* | (2017.01) | |
| *F21V 21/15* | (2006.01) | |
| *F21Y 103/37* | (2016.01) | |

(52) U.S. Cl.
CPC ......... *G01N 21/8806* (2013.01); *F21V 21/15* (2013.01); *G01N 21/8851* (2013.01); *G06T 7/0004* (2013.01); *F21Y 2103/37* (2016.08); *G01N 2021/8835* (2013.01); *G06T 2207/10152* (2013.01)

(58) Field of Classification Search
CPC ........... G01N 21/8806; G01N 21/8851; G01N 2201/062; G01N 21/95684; G06T 7/0004; F21V 21/15; F21Y 2103/37
See application file for complete search history.

(56) References Cited

U.S. PATENT DOCUMENTS

| | | | | |
|---|---|---|---|---|
| 5,461,417 A | * | 10/1995 | White | ............... G01N 21/8806 348/125 |
| 6,788,411 B1 | * | 9/2004 | Lebens | .................. G01N 21/21 356/364 |
| 2007/0097686 A1 | | 5/2007 | Dunn et al. | |
| 2008/0093538 A1 | * | 4/2008 | Diehr | .................... B07C 5/3408 250/223 B |
| 2014/0177932 A1 | * | 6/2014 | Milne | ................ G01N 21/9027 382/128 |

(Continued)

FOREIGN PATENT DOCUMENTS

| | | |
|---|---|---|
| JP | 09133636 A | 5/1997 |
| JP | 2000137000 A | 5/2000 |

(Continued)

OTHER PUBLICATIONS

Communication dated Sep. 18, 2018 from the Japanese Patent Office in counterpart application No. 2016-202444.

*Primary Examiner* — Neil R Mikeska
(74) *Attorney, Agent, or Firm* — Sughrue Mion, PLLC

(57) ABSTRACT

An inspection apparatus includes an illumination device including an arch-like lighting unit that is provided around an inspection target in a circular arc form and emits light toward the inspection target, imaging devices that capture images of a light reflection surface of the inspection target by which the light emitted from the arch-like lighting unit is reflected, and a determination device that inspects the light reflection surface of the inspection target on the basis of the images captured by the imaging devices. As a result, the inspection apparatus provides an effect of preventing the apparatus from being increased in size.

9 Claims, 7 Drawing Sheets

(56) References Cited

U.S. PATENT DOCUMENTS

| | | | |
|---|---|---|---|
| 2014/0376003 A1* | 12/2014 | Keranen | G01B 11/245 |
| | | | 356/610 |
| 2016/0267647 A1* | 9/2016 | Higo | G06T 7/0004 |
| 2016/0282811 A1* | 9/2016 | Urbach | G03H 1/0465 |
| 2017/0108449 A1* | 4/2017 | Wingfield | G01N 21/4788 |
| 2017/0307544 A1* | 10/2017 | Nagata | G01N 21/88 |
| 2017/0343482 A1* | 11/2017 | Kaupp | G01N 21/8806 |
| 2018/0330489 A1* | 11/2018 | Kido | G06T 7/0004 |

FOREIGN PATENT DOCUMENTS

| | | |
|---|---|---|
| JP | 2002221497 A | 8/2002 |
| JP | 2002310935 A | 10/2002 |
| JP | 2005337853 A | 12/2005 |
| JP | 2007183225 A | 7/2007 |
| JP | 2010091530 A | 4/2010 |
| JP | 3169520 U | 8/2011 |
| JP | 2012013509 A | 1/2012 |
| JP | 2014-163874 A | 9/2014 |

* cited by examiner

INSPECTION APPARATUS

CROSS-REFERENCE TO RELATED APPLICATION(S)

The present application claims priority to and incorporates by reference the entire contents of Japanese Patent Application No. 2016-202444 filed in Japan on Oct. 14, 2016.

BACKGROUND OF THE INVENTION

1. Field of the Invention

The present invention relates to an inspection apparatus.

2. Description of the Related Art

As a conventional inspection apparatus that inspects an outer appearance of a surface of an inspection target, for example, Japanese Patent Application Laid-open No. 2014-163874 discloses an inspection apparatus including an inspection table on which a connector component as the inspection target is placed, a lighting body that emits light to the connector component, and a camera that captures an image of the connector component while setting an optical axis thereof to a direction oblique to a horizontal plane, the direction enabling three surfaces of the connector component to be shot, wherein an image capturing surface of the camera is inclined with respect to the optical axis.

The above-mentioned inspection apparatus disclosed in Japanese Patent Application Laid-open No. 2014-163874 has a room for further improvement in preventing the apparatus from being increased in size in order to enable inspection to be performed in a limited space on, for example, a manufacturing line.

SUMMARY OF THE INVENTION

The present invention has been made in view of the above-described circumstances and an object thereof is to provide an inspection apparatus capable of preventing the apparatus from being increased in size.

In order to achieve the above mentioned object, an inspection apparatus according to one aspect of the present invention includes an illumination device including an arch-like lighting unit that is provided around an inspection target in a circular arc form and emits light toward the inspection target; an imaging device configured to capture an image of a light reflection surface of the inspection target by which the light emitted from the arch-like lighting unit is reflected; and a determination device configured to inspect the light reflection surface of the inspection target on the basis of the image captured by the imaging device.

According to another aspect of the present invention, in the inspection apparatus, it is preferable that the inspection apparatus further includes a rotation driving device that relatively rotates the inspection target and the arch-like lighting unit about a rotating axial line along a line connecting both end portions of the arch-like lighting unit as a rotating center, wherein the determination device inspects the light reflection surface of the inspection target on the basis of the image captured by the imaging device while relatively rotating the inspection target and the arch-like lighting unit by the rotation driving device.

According to still another aspect of the present invention, in the inspection apparatus, it is preferable that the inspection apparatus further includes a holding surface configured to hold the inspection target in a height direction, wherein at least end portions of the light reflection surface of the inspection target are formed into curved surface, both end portions of the arch-like lighting unit are located on an opposite side to the inspection target with respect to the holding surface in the height direction, and the rotation driving device rotates the arch-like lighting unit from a start position at which a top portion of the circular arc form of the arch-like lighting unit is located on an opposite side to the inspection target with respect to the holding surface in the height direction to an end position at which the top portion is located on an opposite side to the inspection target with respect to the holding surface, the end position being on an opposite side to the start position in a direction of scanning of the inspection target with the light by the arch-like lighting unit with the relative rotation of the inspection target and the arch-like lighting unit.

According to still another aspect of the present invention, in the inspection apparatus, it is preferable that at least one imaging device is provided on both sides of the rotating axial line in a direction of scanning of the inspection target with the light by the arch-like lighting unit with the relative rotation of the inspection target and the arch-like lighting unit, and each imaging device is located on an opposite side to the inspection target with respect to the arch-like lighting unit and a position of each imaging device relative to the inspection target is fixed.

According to still another aspect of the present invention, in the inspection apparatus, it is preferable that the imaging device captures an image of the light reflection surface of the inspection target a plurality of number of times with the relative rotation of the inspection target and the arch-like lighting unit, and the determination device inspects gloss abnormality of the light reflection surface of the inspection target on the basis of the images captured by the imaging device with the relative rotation of the inspection target and the arch-like lighting unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, an embodiment according to the present invention will be described in detail with reference to the drawings. It should be noted that the embodiment does not limit this invention. Components in the following embodiment include components by which those skilled in the art can replace or substantially the same components.

Embodiment

Figure 1:
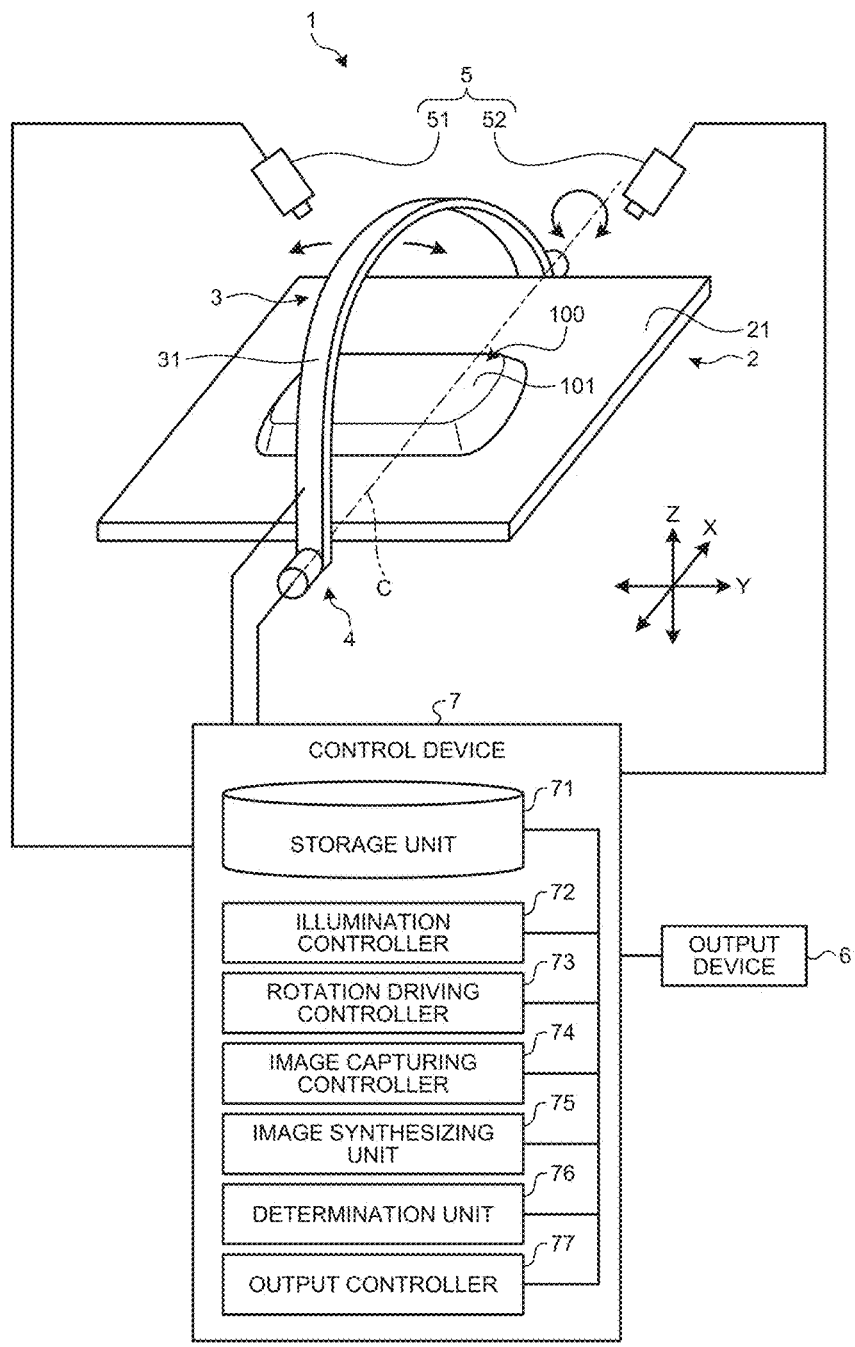
FIG. 1 is a schematic block diagram illustrating the schematic configuration of an inspection apparatus according to an embodiment.
Figure 2:
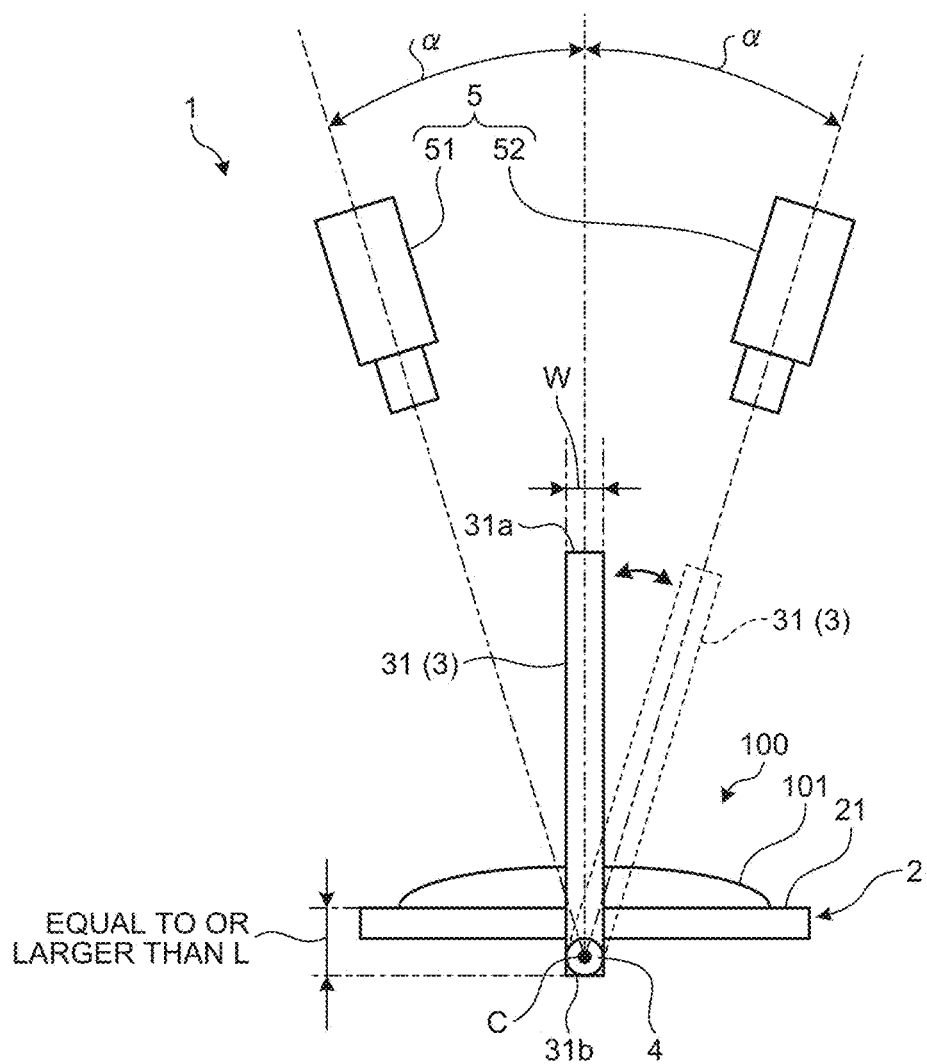
FIG. 2 is a schematic front view illustrating respective parts of the inspection apparatus in the embodiment when seen from one side in the direction of a rotating axial line.
Figure 3:
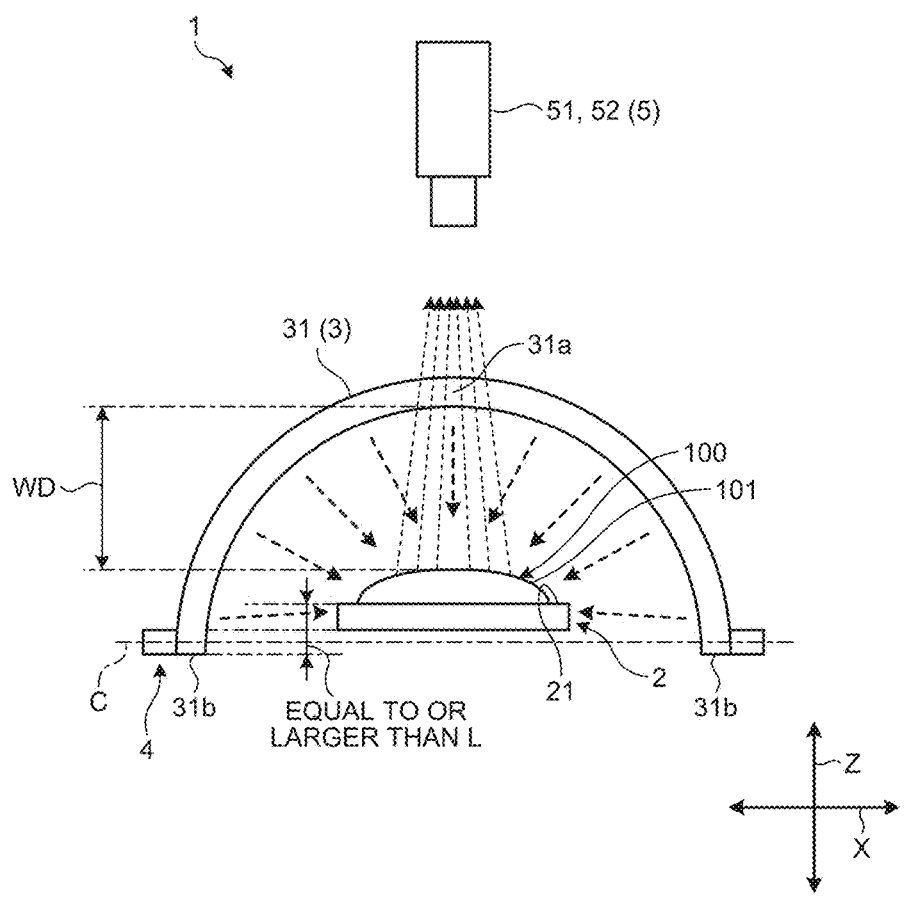
FIG. 3 is a schematic front view illustrating the respective parts of the inspection apparatus in the embodiment when seen from one side in the scanning direction.

An inspection apparatus 1 according to the embodiment, which is illustrated in FIG. 1, FIG. 2, and FIG. 3, inspects an outer appearance of a light reflection surface 101 forming the surface of an inspection target 100, and typically inspects gloss abnormality of the light reflection surface 101 of the inspection target 100. The inspection target 100 has a gloss surface formed by the light reflection surface 101 on the front surface thereof and is, for example, a metal component or a resin molded product. The inspection target 100 in the embodiment is the resin molded product in which at least end portions of the light reflection surface 101 are formed into curved surfaces and that has light transmittance, and as an example, is a room lamp cover that is provided in a cabin of a vehicle. Hereinafter, the configuration of the inspection apparatus 1 will be described in detail with reference to the respective drawings.

In the following description, a first direction is referred to as a "rotating axis direction X", a second direction is referred to as a "scanning direction Y", and a third direction is referred to as a "height direction Z" among the first direction, the second direction, and the third direction that intersect with one another. The rotating axis direction X, the scanning direction Y, and the height direction Z are orthogonal to (intersect with) one another. The rotating axis direction X typically corresponds to a direction along a rotating axial line C of an arch-like lighting unit 31, which will be described later. The scanning direction Y corresponds to a direction of scanning that is performed on the inspection target 100 with light by the arch-like lighting unit 31 with relative rotation of the inspection target 100 and the arch-like lighting unit 31. The height direction Z corresponds to the thickness direction of the inspection target 100 that a holding surface 21, which will be described later, holds, and typically corresponds to a normal line direction of the holding surface 21 formed as a flat surface. The height direction Z in the embodiment is typically a vertical direction, and the rotating axis direction X and the scanning direction Y are horizontal directions. The respective directions that are used in the following description indicate directions in a state in which the respective parts are assembled on one another unless otherwise specified.

To be specific, the inspection apparatus 1 in the embodiment includes a placement table 2, an illumination device 3, a rotation driving device 4, imaging devices 5, an output device 6, and a control device 7 as a determination device, as illustrated in FIG. 1, FIG. 2, and FIG. 3.

The placement table 2 has the holding surface 21 holding the inspection target 100 in the height direction Z. Although the placement table 2 is formed to have a rectangular plate shape in the drawings, it is not limited to have this shape. The holding surface 21 is provided as the surface of the placement table 2 on one side in the height direction Z. In this example, the holding surface 21 is provided as the surface thereof on the upper side in the vertical direction. The holding surface 21 in the embodiment is formed as a flat surface the normal line direction of which is along the height direction Z, that is, is formed as a horizontal surface, and configures a placement surface holding the inspection target 100 by placing the inspection target 100 thereon in the vertical direction (height direction Z).

The illumination device 3 emits light for inspection (hereinafter, referred to as "inspection light" in some cases) to the inspection target 100 held on the holding surface 21. The illumination device 3 in the embodiment includes the arch-like lighting unit 31. The arch-like lighting unit 31 is provided around the inspection target 100 in a circular arc form and emits the inspection light toward the light reflection surface 101 of the inspection target 100. The arch-like lighting unit 31 is configured by aligning a plurality of light emitting elements such as light emitting diodes (LEDs) in a circular arc form and holding them in a housing or the like. The arch-like lighting unit 31 is provided so as to surround a part of the surrounding of the inspection target 100 with such positional relation that the inspection target 100 held on the holding surface 21 is located on the inner side of the light emitting elements aligned in the circular arc form. The arch-like lighting unit 31 may be configured by aligning the light emitting elements in a circular arc form (for example, semicircular arc form) formed by a single circular arc (that is, circular arc with a single radius) or aligning the light emitting elements in a circular arc form formed by combining a plurality of circular arcs (that is, circular arcs with different radii). The arch-like lighting unit 31 in the embodiment is arranged so as to have a predetermined positional relation with the holding surface 21 holding the inspection target 100 in order to properly emit the inspection light to the entire surface of the light reflection surface 101 of the inspection target 100, the end portions of the light reflection surface 101 being formed into the curved surfaces. That is to say, both end portions 31b of the arch-like lighting unit 31 are located on the opposite side to the inspection target 100 with respect to the holding surface 21 in the height direction Z. In other words, the end portions 31b of the arch-like lighting unit 31 are located on the lower side than the holding surface 21 in the vertical direction. The illumination device 3 emits the inspection light toward the inspection target 100 from the arch-like lighting unit 31 by emitting the inspection light toward the inner side of the circular arc from the light emitting elements configuring the arch-like lighting unit 31. The illumination device 3 may include a diffusion plate that diffuses the inspection light emitted from the light emitting elements toward the inspection target 100. The illumination device 3 may include light shielding hoods on both sides of the light emitting elements in the scanning direction Y to reduce stray light by irregular reflection. The illumination device 3 includes, in addition to the arch-like lighting unit 31, for example, a driving circuit for driving the arch-like lighting unit 31. The driving circuit and the like of the illumination device 3 are electrically connected to the control device 7 and driving of the respective parts thereof is controlled on the basis of control signals input from the control device 7.

The rotation driving device 4 relatively rotates the inspection target 100 and the arch-like lighting unit 31 about the rotating axial line C as a rotating center. The rotating axial line C is an axial line as the rotating center of the relative rotation of the inspection target 100 and the arch-like lighting unit 31 and is an axial line along a line connecting the end portions of the arch-like lighting unit 31. The rotating axial line C is set along the rotating axis direction X. The rotation driving device 4 in the embodiment relatively rotates the inspection target 100 and the arch-like lighting unit 31 by rotating the arch-like lighting unit 31 about the rotating axial line C relatively to the holding surface 21 holding the inspection target 100. The rotation driving device 4 supports the arch-like lighting unit 31 with respect to the placement table 2, a structure on which the placement table 2 is provided, or the like so as to enable the arch-like lighting unit 31 to rotate about the above-mentioned rotating axial line C. The rotation driving device 4 rotates the arch-like lighting unit 31 to an end position from a predetermined start position while passing through an upper side of the inspection target 100 in the vertical direction (side at which the light reflection surface 101 is located in the height direction Z). The predetermined start position is a position at which a top portion 31a of the circular arc form of the arch-like lighting unit 31 is located on the opposite side to the inspection target 100 with respect to the holding surface 21 in the height direction Z, that is, on the lower side relative to the holding surface 21 in the vertical direction. On the other hand, the predetermined end position is a position on the opposite side to the start position in the scanning direction Y, and the top portion 31a is located on the opposite side to the inspection target 100 with respect to the holding surface 21, that is, on the lower side relative to the holding surface 21 in the vertical direction. The rotation driving device 4 includes a motor as a driving source for rotating the arch-like lighting unit 31, a rotating mechanism rotating the arch-like lighting unit 31 with a driving force generated by the motor, a transmission member transmitting the driving force generated by the motor to the rotating mechanism, such as a transmission gear and a transmission belt, and a driving circuit for driving the rotation driving device 4. The driving circuit and the like of the rotation driving device 4 are electrically connected to the control device 7 and driving of the respective parts is controlled on the basis of control signals input from the control device 7.

The imaging devices 5 capture images of the light reflection surface 101 of the inspection target 100 by which the inspection light emitted from the arch-like lighting unit 31 is reflected. As the imaging devices 5, for example, CCD cameras or CMOS cameras can be used. At least one imaging device 5 in the embodiment is provided on each of the sides of the rotating axial line C in the scanning direction Y of the scanning that is performed on the inspection target 100 with the light by the arch-like lighting unit 31 with the relative rotation of the inspection target 100 and the arch-like lighting unit 31. The imaging devices 5 include a first camera 51 and a second camera 52. The first camera 51 is provided on one side of the rotating axial line C and the second camera 52 is provided on the other side of the rotating axial line C in the scanning direction Y. The first camera 51 and the second camera 52 are located on the opposite side to the inspection target 100 with respect to the arch-like lighting unit 31, that is, on the outer side of the arch-like lighting unit 31, and the positions thereof relative to the inspection target 100 are fixed. The first camera 51 and the second camera 52 are fixedly supported on, for example, the placement table 2 or the structure on which the placement table 2 is provided through a support frame or the like, so that the positions thereof relative to the inspection target 100 are fixed on the outer side of the arch-like lighting unit 31. The first camera 51 and the second camera 52 are arranged such that optical axes thereof are directed to the light reflection surface 101 of the inspection target 100 in a state in which the positions thereof relative to the inspection target 100 are fixed and image capturing view angles thereof cover the entire light reflection surface 101. That is to say, the first camera 51 and the second camera 52 are arranged in such a manner as to respectively capture the entire images of the light reflection surface 101. The respective optical axis angles (camera attach angles) α (see FIG. 2) of the first camera 51 and the second camera 52 are preferably set to, for example, approximately equal to or larger than 5° and equal to or smaller than 30° (5°≤α≤30° but are not limited thereto and may be, for example, 0°. The respective optical axis angles α correspond to angles formed by the optical axes of the first camera 51 and the second camera 52 and the normal line of the holding surface 21. The first camera 51 and the second camera 52 respectively include driving circuits for driving the first camera 51 and the second camera 52. The driving circuits and the like of the first camera 51 and the second camera 52 are electrically connected to the control device 7 and driving of the respective parts is controlled on the basis of control signals input from the control device 7. The first camera 51 and the second camera 52 can respectively output pieces of image data of the captured images to the control device 7. In the following description, when the first camera 51 and the second camera 52 need not to be particularly distinguished from each other for description, they are simply referred to as the "imaging devices 5".

The output device 6 outputs various pieces of information related to a result of inspection in the inspection apparatus 1. As the output device 6, for example, a display or a display light for outputting visual information (image information, character information, and the like) as the various pieces of information related to the result of the inspection, a speaker for outputting auditory information (audio information and sound information) as the various pieces of information, or the like can be employed. The output device 6 includes a driving circuit for driving the output device 6. The driving circuit and the like of the output device 6 are electrically connected to the control device 7 and driving of the respective parts thereof is controlled on the basis of control signals input from the control device 7.

The control device 7 configures the determination device that inspects the light reflection surface 101 of the inspection target 100 on the basis of the images captured by the imaging devices 5. Although the control device 7 that comprehensively controls the respective parts of the inspection apparatus 1 also functions as the determination device in the embodiment, the determination device is not limited thereto. The determination device may be configured separately from the control device 7 and transmit and receive various signals and various pieces of information to and from the control device 7. The control device 7 includes an electronic circuit configured by, as a main body, a well-known microcomputer with a central processing unit (CPU), a read only memory (ROM), a random access memory (RAM), and an interface. The control device 7 is electrically connected to the illumination device 3, the rotation driving device 4, the imaging devices 5, the output device 6, and the like through the driving circuits and the like thereof and outputs the control signals to the illumination device 3, the rotation driving device 4, the imaging devices 5, the output device 6, and the like. The pieces of image data of the images captured by the first camera 51 and the second camera 52 are input to the control device 7. The control device 7 executes control programs stored in the ROM, the RAM, or the like to output the control signals to the illumination device 3, the rotation driving device 4, the imaging devices 5, the output device 6, and the like and execute various pieces of processing for inspecting the light reflection surface 101 of the inspection target 100.

The control device 7 in the embodiment inspects the light reflection surface 101 of the inspection target 100 on the basis of the images captured by the imaging devices 5 while relatively rotating the inspection target 100 and the arch-like lighting unit 31 by the rotation driving device 4. In this case, the imaging devices 5 capture images of the light reflection surface 101 of the inspection target 100 a plurality of number of times with the relative rotation of the inspection target 100 and the arch-like lighting unit 31 on the basis of the control by the control device 7 and output the captured images to the control device 7. The control device 7 inspects gloss abnormality of the light reflection surface 101 of the inspection target 100 on the basis of the images captured by the imaging devices 5 with the relative rotation of the inspection target 100 and the arch-like lighting unit 31.

The control device 7 includes, as an example, a storage unit 71, an illumination controller 72, a rotation driving controller 73, an image capturing controller 74, an image synthesizing unit 75, a determination unit 76, and an output controller 77 functionally conceptually. The storage unit 71, the illumination controller 72, the rotation driving controller 73, the image capturing controller 74, the image synthesizing unit 75, the determination unit 76, and the output controller 77 can transmit and receive various signals and various pieces of information to and from various devices that are electrically connected thereto.

The storage unit 71 is a storage device such as a memory and stores therein conditions and pieces of data that are necessary for various pieces of processing in the control device 7, various computer programs that are executed in the control device 7, and the like. Furthermore, the storage unit 71 stores therein pieces of image data indicating the images captured by the imaging devices 5 and input to the control device 7.

The illumination controller 72 outputs control signals to the illumination device 3 and executes processing of controlling driving of the arch-like lighting unit 31 of the illumination device 3. The illumination controller 72 executes the various computer programs stored in the storage unit 71 and thereby controls driving of the arch-like lighting unit 31 to turn the arch-like lighting unit 31 on and off.

The rotation driving controller 73 outputs control signals to the rotation driving device 4 and executes processing of controlling driving of the rotation driving device 4. The rotation driving controller 73 executes the various computer programs stored in the storage unit 71 and thereby controls driving of the rotation driving device 4 to rotate the arch-like lighting unit 31 about the rotating axial line C as the rotating center relatively to the inspection target 100. In the inspection, the rotation driving controller 73, for example, controls the rotation driving device 4 to rotate the arch-like lighting unit 31 from the start position at which the top portion 31*a* of the arch-like lighting unit 31 is located on the lower side relative to the holding surface 21 in the vertical direction to the end position at which on the opposite side to the start position in the scanning direction Y, the top portion 31*a* is located on the lower side relative to the holding surface 21 in the vertical direction.

The control device 7 turns on the arch-like lighting unit 31 on the basis of the control by the above-mentioned illumination controller 72 and drives the rotation driving device 4 to rotate the arch-like lighting unit 31 relatively to the inspection target 100 on the basis of the above-mentioned control by the rotation driving controller 73. The control device 7 can therefore scan the light reflection surface 101 of the inspection target 100 with the inspection light from the arch-like lighting unit 31 along the scanning direction Y.

The image capturing controller 74 outputs control signals to the imaging devices 5 and executes processing of controlling driving of the imaging devices 5. The image capturing controller 74 executes the various computer programs stored in the storage unit 71 and thereby controls driving of the imaging devices 5 to capture the images of the light reflection surface 101 of the inspection target 100 while rotating the arch-like lighting unit 31 relatively to the inspection target 100. The image capturing controller 74 controls the imaging devices 5 to continuously capture the images of the light reflection surface 101 of the inspection target 100 a number of times with the relative rotation of the inspection target 100 and the arch-like lighting unit 31. The image capturing controller 74 causes each of the first camera 51 and the second camera 52 to continuously capture the images of the light reflection surface 101 of the inspection target 100 a number of times with the relative rotation of the inspection target 100 and the arch-like lighting unit 31. The control device 7 can therefore control to continuously capture the images of the light reflection surface 101 of the inspection target 100 a number of times on the basis of the above-mentioned control by the image capturing controller 74 while scanning the light reflection surface 101 with the inspection light from the arch-like lighting unit 31 along the scanning direction Y. Then, the image capturing controller 74 controls the imaging devices 5 to store the captured images in the storage unit 71.

Figure 4:
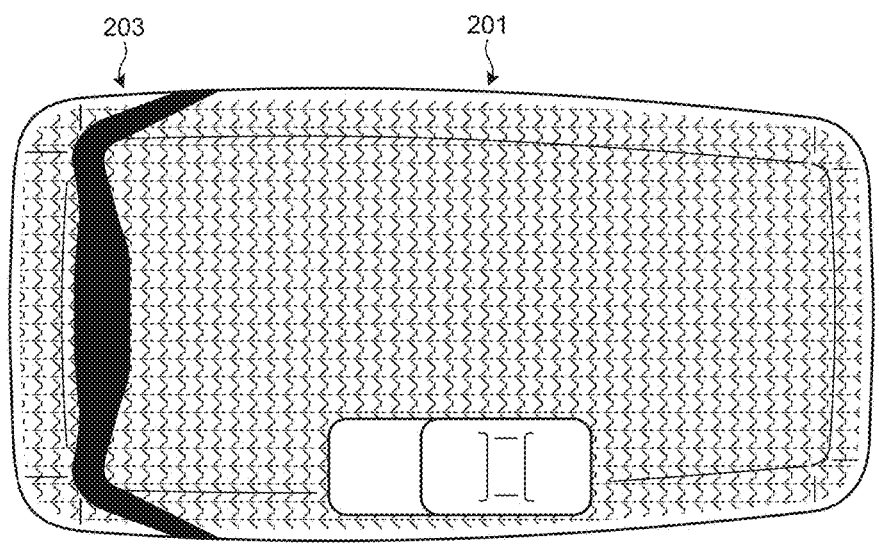
FIG. 4 is a schematic view illustrating an example of a synthesized image in the inspection apparatus in the embodiment.
Figure 5:
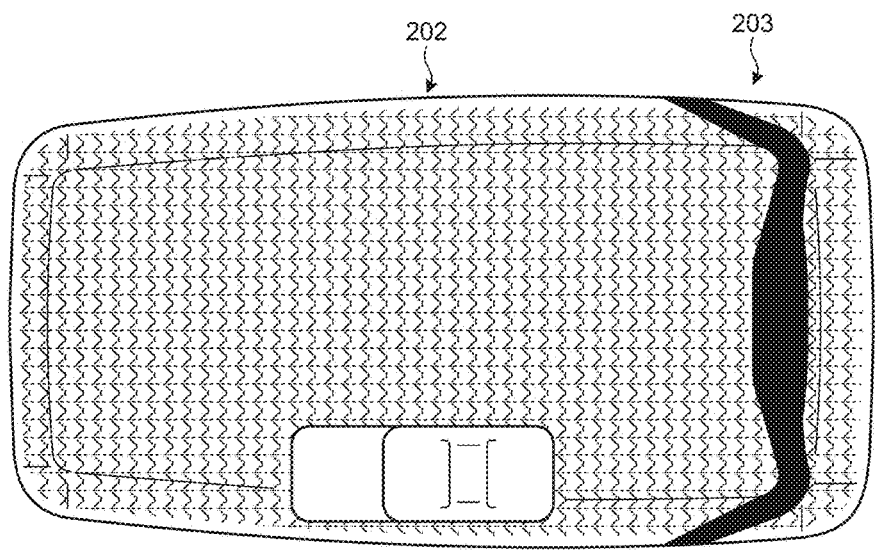
FIG. 5 is a schematic view illustrating another example of the synthesized image in the inspection apparatus in the embodiment.

The image synthesizing unit 75 executes various pieces of image processing on the images captured by the imaging devices 5 and stored in the storage unit 71. The images that are stored in the storage unit 71 and on which the image synthesizing unit 75 performs the pieces of image processing are the images of the light reflection surface 101 of the inspection target 100 that have been continuously captured while scanning the light reflection surface 101 with the inspection light from the arch-like lighting unit 31 along the scanning direction Y. The image synthesizing unit 75 executes the pieces of image processing on the images of the light reflection surface 101 of the inspection target 100 that have been continuously captured while scanning the light reflection surface 101 with the inspection light from the arch-like lighting unit 31 along the scanning direction Y to generate two-dimensional images formed by synthesizing the images. The image synthesizing unit 75 executes the various computer programs stored in the storage unit 71 and thereby executes the pieces of image processing on the images of the light reflection surface 101 that are stored in the storage unit 71 to generate the two-dimensional images. The image synthesizing unit 75 in the embodiment extracts regions the brightness of which is higher than a predetermined threshold from the images of the light reflection surface 101 and connects and synthesizes the extracted regions in order along the scanning direction Y to generate synthesized images 201 and 202 as illustrated in FIG. 4 and FIG. 5. The synthesized images 201 and 202 are provided by extracting regions in which the inspection light from the arch-like lighting unit 31 is reflected from the images of the light reflection surface 101 of the inspection target 100 that have been continuously captured while scanning the light reflection surface 101 with the inspection light along the scanning direction Y, and synthesizing them. The image synthesizing unit 75 executes the above-mentioned pieces of image processing on both of the images of the light reflection surface 101 that have been captured by the first camera 51 and the images of the light reflection surface 101 that have been captured by the second camera 52. For example, the image synthesizing unit 75 synthesizes the images of the light reflection surface 101 that have been captured by the first camera 51 to generate the synthesized image 201 illustrated in FIG. 4 and synthesizes the images of the light reflection surface 101 that have been captured by the second camera 52 to generate the synthesized image 202 illustrated in FIG. 5. The image synthesizing unit 75 stores the generated synthesized images 201 and 202 in the storage unit 71.

As described above, the first camera 51 and the second camera 52 are located on the opposite side to the inspection target 100 with respect to the arch-like lighting unit 31, that is, on the outer side of the arch-like lighting unit 31, and the positions thereof relative to the inspection target 100 are fixed. With this arrangement manner, in the inspection apparatus 1, when the arch-like lighting unit 31 is made to rotate relatively to the inspection target 100 in order to scan the light reflection surface 101 with the inspection light along the scanning direction Y, the arch-like lighting unit 31 crosses between the first camera 51 and the second camera 52 and the light reflection surface 101. Each of the synthesized images 201 and 202 therefore contains a dead angle image 203 corresponding to a dead angle formed when the arch-like lighting unit 31 crosses between each of the first camera 51 and the second camera 52 and the light reflection surface 101. To cope with this dead angle images, the inspection apparatus 1 has the configuration in which the first camera 51 is provided on one side and the second camera 52 are provided on the other side with respect to the rotating axial line C in the scanning direction Y as described above. With this configuration, the synthesized image 201 based on the images captured by the first camera 51 and the synthesized image 202 based on the images captured by the second camera 52 have a relation of mutually complementing images in the regions of the light reflection surface 101 that correspond to the respective dead angle images 203.

Figure 6:
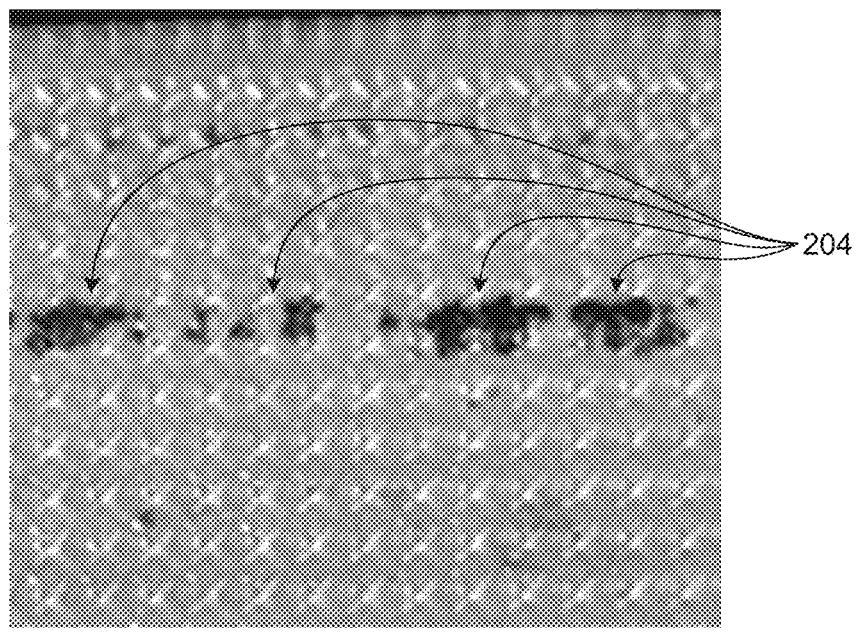
FIG. 6 is a view illustrating an example of an image of gloss abnormal sites in the inspection apparatus in the embodiment.

The determination unit 76 executes processing of inspecting the light reflection surface 101 of the inspection target 100 on the basis of the synthesized images 201 and 202 synthesized by the image synthesizing unit 75. The determination unit 76 executes the various computer programs stored in the storage unit 71 and thereby determines gloss abnormality of the light reflection surface 101 of the inspection target 100 on the basis of the synthesized images 201 and 202. The determination unit 76 extracts regions with relatively low brightness and regions with uneven brightness as gloss abnormal sites 204 from the synthesized images 201 and 202, as illustrated in FIG. 6. The determination unit 76 determines that the gloss of the light reflection surface 101 is normal when no gloss abnormal site 204 is extracted. On the other hand, the determination unit 76 determines that the gloss of the light reflection surface 101 is abnormal when the gloss abnormal site 204 is extracted.

The output controller 77 outputs control signals to the output device 6 and executes processing of controlling driving of the output device 6. The output controller 77 executes the various computer programs stored in the storage unit 71 and thereby controls driving of the output device 6 to output various pieces of information related to the result of the inspection by the determination unit 76. The output controller 77 controls the output device 6 to notify a user of determination indicating that the gloss of the light reflection surface 101 is abnormal when, for example, the determination unit 76 extracts the gloss abnormal site 204 and determines that the gloss of the light reflection surface 101 is abnormal. The output device 6 may notify the user of the determination indicating that the gloss of the light reflection surface 101 is abnormal by, for example, displaying an image containing the gloss abnormal site 204 on the display or flashing the display light. The output device 6 may notify the user of the determination indicating that the gloss of the light reflection surface 101 is abnormal by, for example, outputting audio information, warning sound, or the like with the speaker.

Figure 7:
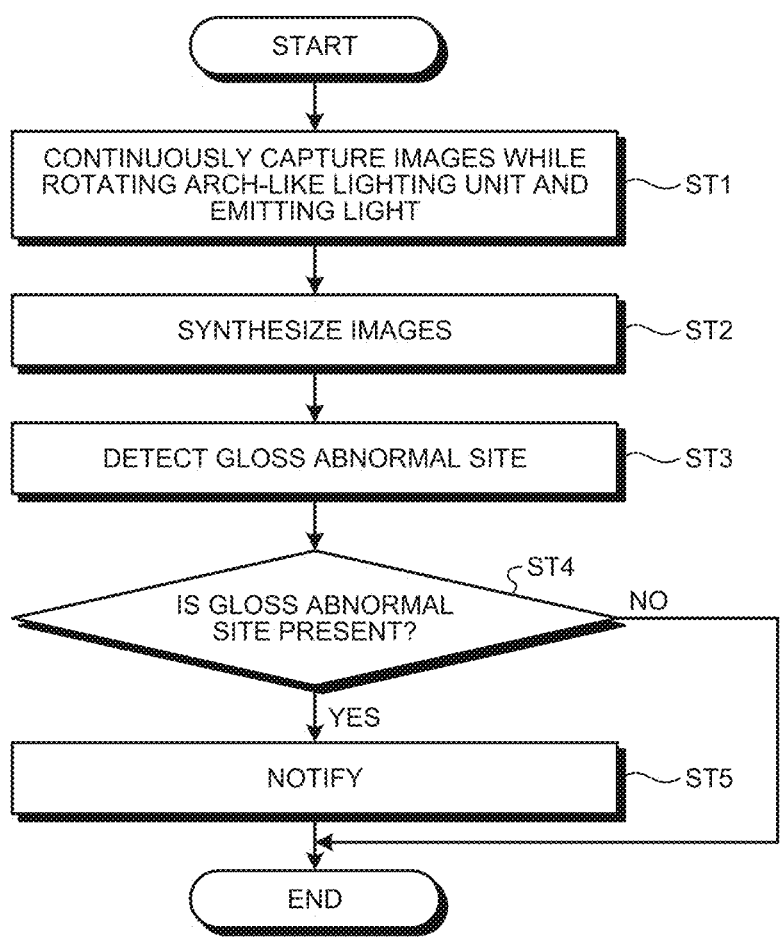
FIG. 7 is a flowchart illustrating an example of control in the inspection apparatus in the embodiment.

Next, an example of control in the inspection apparatus 1 will be described with reference to a flowchart in FIG. 7.

First, the control device 7 emits the inspection light to the inspection target 100 from the arch-like lighting unit 31 on the basis of control by the illumination controller 72 while driving the rotation driving device 4 to rotate the arch-like lighting unit 31 relatively to the inspection target 100 on the basis of control by the rotation driving controller 73. Then, the control device 7 controls the imaging devices 5 on the basis of control by the image capturing controller 74 to continuously capture the images of the light reflection surface 101 of the inspection target 100 (step ST1). The image capturing controller 74 controls to store the captured images in the storage unit 71.

Thereafter, the image synthesizing unit 75 of the control device 7 executes the pieces of image processing on the images captured by the imaging devices 5 at step ST1 and stored in the storage unit 71 to generate synthesized images (step ST2). That is to say, the image synthesizing unit 75 extracts regions the brightness of which is higher than the predetermined threshold from the images of the light reflection surface 101 that are stored in the storage unit 71 and connects and synthesizes the extracted regions in order along the scanning direction Y to generate, for example, the synthesized images 201 and 202 as illustrated in FIG. 4 and FIG. 5.

Subsequently, the determination unit 76 of the control device 7 extracts the gloss abnormal site 204 from the synthesized images 201 and 202 on the basis of the synthesized images 201 and 202 synthesized by the image synthesizing unit 75 at step ST2 (step ST3).

Then, the determination unit 76 determines whether the gloss abnormal site 204 has been extracted at step ST3 (step ST4).

When the determination unit 76 determines that the gloss abnormal site 204 has been extracted at step ST4 (Yes at step ST4), the output controller 77 of the control device 7 controls the output device 6 to notify a user of determination indicating that the gloss of the light reflection surface 101 is abnormal (step ST5) and finishes this control. When the determination unit 76 determines that no gloss abnormal site 204 has been extracted at step ST4 (No at step ST4), the control device 7 does not perform the processing at step ST5 and finishes this control.

The inspection apparatus 1 configured as described above can adjust balance between inspection accuracy and an operation amount (operation load) in the inspection by adjusting a ratio W/WD of a width W (see FIG. 2) of the arch-like lighting unit 31 along the scanning direction Y and a distance WD (see FIG. 3) to the light reflection surface 101 of the inspection target 100 from the top portion 31a of the arch-like lighting unit 31. In the inspection apparatus 1, the width of the inspection light that is reflected onto the light reflection surface 101 can be relatively decreased by relatively lowering the ratio W/WD, in other words, relatively decreasing the width W or relatively increasing the distance WD. In this case, the inspection apparatus 1 relatively increases the number of times of image capturing of the light reflection surface 101 of the inspection target 100 while scanning the light reflection surface 101 with the inspection light from the arch-like lighting unit 31 along the scanning direction Y in accordance with the width of the inspection light that is reflected onto the light reflection surface 101. The inspection apparatus 1 can thereby relatively increase the number of images configuring the synthesized images 201 and 202 to relatively improve extraction accuracy of the gloss abnormal site 204, thereby enhancing the inspection accuracy of the light reflection surface 101. On the other hand, the inspection apparatus 1 can relatively increase the width of the inspection light that is reflected onto the light reflection surface 101 by relatively increasing the ratio W/WD, in other words, relatively increasing the width W or relatively decreasing the distance WD. In this case, the inspection apparatus 1 relatively decreases the number of times of image capturing of the light reflection surface 101 of the inspection target 100 while scanning the light reflection surface 101 with the inspection light from the arch-like lighting unit 31 along the scanning direction Y in accordance with the width of the inspection light that is reflected onto the light reflection surface 101. The inspection apparatus 1 can thereby relatively decrease the number of images configuring the synthesized images 201 and 202 to reduce the operation amount (operation load) in the inspection, thereby enhancing the inspection efficiency. The inspection apparatus 1 can adjust the balance between the inspection accuracy and the operation amount (operation load) in the inspection by adjusting the ratio W/WD in consideration of the above-described relation.

The inspection apparatus 1 described above can use the illumination device 3, the imaging devices 5, and the control device 7 to emit the inspection light to the light reflection surface 101 of the inspection target 100, capture the images of the light reflection surface 101 of the inspection target 100 by which the inspection light is reflected, and inspect the light reflection surface 101 of the inspection target 100 on the basis of the captured images. In this case, the inspection apparatus 1 has the configuration in which the arch-like lighting unit 31 emitting the inspection light to the light reflection surface 101 of the inspection target 100 is provided around the inspection target 100 in the circular arc form and emits the light toward the inspection target 100, thereby being reduced in size in the rotating axis direction X in comparison with, for example, the case in which a lighting unit emitting inspection light is linearly configured along the rotating axis direction X. As a result, the inspection apparatus 1 can be prevented from being increased in size and inspect the inspection target 100 in a limited space on, for example, a manufacturing line of the inspection target 100.

The inspection apparatus 1 described above can scan the light reflection surface 101 of the inspection target 100 with the inspection light from the arch-like lighting unit 31 along the scanning direction Y by emitting the inspection light to the inspection target 100 from the arch-like lighting unit 31 while driving the rotation driving device 4 to rotate the arch-like lighting unit 31 relatively to the inspection target 100. The inspection apparatus 1 can inspect the light reflection surface 101 of the inspection target 100 on the basis of the images of the light reflection surface 101 that have been continuously captured by the imaging devices 5 while scanning the light reflection surface 101 of the inspection target 100 with the inspection light from the arch-like lighting unit 31 along the scanning direction Y. The inspection apparatus 1 can be prevented from being increased in size even when performing the above-mentioned inspection.

To be more specific, the inspection apparatus 1 described above can synthesize the images of the light reflection surface 101 of the inspection target 100 that have been continuously captured by the imaging devices 5 while scanning the light reflection surface 101 with the inspection light from the arch-like lighting unit 31 along the scanning direction Y and inspect the gloss abnormality of the light reflection surface 101 on the basis of the synthesized images. Even in this case, the inspection apparatus 1 can be prevented from being increased in size as described above.

In the inspection apparatus 1 described above, the end portions 31b of the arch-like lighting unit 31 are located on the opposite side to the inspection target 100 with respect to the holding surface 21 in the height direction Z and the rotation driving device 4 rotates the arch-like lighting unit 31 to the end position from the start position in the above-mentioned inspection. Both of the start position and the end position of the rotation of the arch-like lighting unit 31 are the positions at which the top portion 31a of the arch-like lighting unit 31 is located on the opposite side to the inspection target 100 with respect to the holding surface 21 in the height direction Z. With this arrangement, in the inspection apparatus 1, even when the end portions of the light reflection surface 101 of the inspection target 100 are formed into the curved surfaces, the arch-like lighting unit 31 can reliably emit the inspection light to the entire surface to the ends of the light reflection surface 101 that are formed into the curved surfaces for inspection, thereby improving the inspection accuracy while preventing the apparatus from being increased in size.

Figure 8:
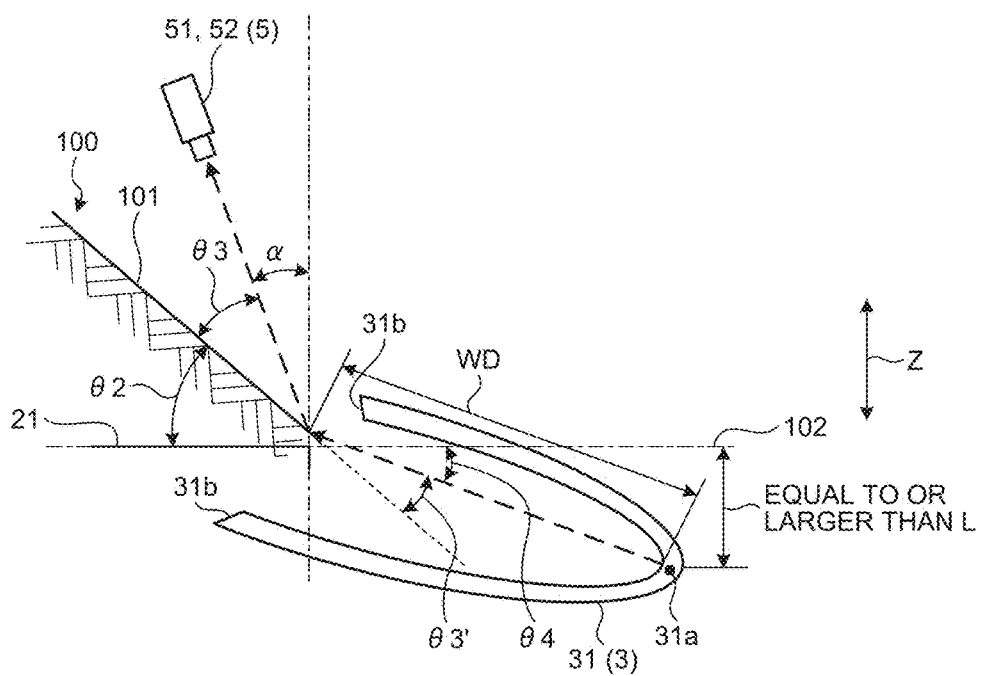
FIG. 8 is a schematic view for explaining positions of end portions of an arch-shaped lighting unit of the inspection apparatus in the embodiment.

In this case, in the inspection apparatus 1, typically, the arch-like lighting unit 31 is preferably arranged such that the distance between an end portion position 102 of the light reflection surface 101 on the holding surface 21 side in the height direction Z and the position of the end portions 31b of the arch-like lighting unit 31 along the height direction Z is equal to or larger than a predetermined set distance L, as illustrated in FIG. 2, FIG. 3, and FIG. 8. In the same manner, in the inspection apparatus 1, as illustrated in FIG. 8, the arch-like lighting unit 31 is preferably arranged such that the distance between the position of the top portion 31a at the start position and the end position of the rotation of the arch-like lighting unit 31 and the end portion position 102 in the height direction Z is equal to or larger than the set distance L. The set distance L is typically defined by the optical axis angle α formed by the optical axes of the first camera 51 and the second camera 52 and the normal line of the holding surface 21, the distance WD to the light reflection surface 101 of the inspection target 100 from the top portion 31a of the arch-like lighting unit 31, a surface tangent angle θ2 formed by a surface tangent line of the light reflection surface 101 of the inspection target 100 and the holding surface 21, and the like as illustrated in FIG. 8. The set distance L [mm] can be expressed by the following equation (1) using the optical axis angle α [°], the distance WD [mm], and the surface tangent angle θ2 [°]. An application angle of the surface tangent angle θ2 is supposed to be, for example, approximately equal to or larger than 0° and equal to or smaller than 45° (0°≤θ2≤45°).

$$L = WD \cdot \mathrm{Sin}(2 \cdot \theta2 + \alpha - 90) \qquad (1)$$

In FIG. 8, an angle θ3' [°] is an incident angle of the inspection light on the light reflection surface 101 and an angle θ3[°] is a reflection angle of the inspection light by the light reflection surface 101. In this case, the above-mentioned equation (1) can be derived on the basis of relational expressions indicated by the following equations (2) to (5) that are satisfied.

$$L = WD \cdot \sin(\theta 4) \quad (2)$$

$$\theta 4 = \theta 2 - \theta 3' \quad (3)$$

$$\theta 3' = \theta 3 \quad (4)$$

$$\theta 3 = 90 - \alpha - \theta 2 \quad (5)$$

The arch-like lighting unit 31 is arranged with the above-mentioned geometric positional relation on the basis of the above-described set distance L, thereby reliably emitting the inspection light across the entire surface to the ends of the light reflection surface 101 of the inspection target 100 that are formed into the curved surfaces.

In the inspection apparatus 1 described above, at least one imaging device 5 is provided on each of the sides of the rotating axial line C as the rotating center of the relative rotation of the inspection target 100 and the arch-like lighting unit 31. With this arrangement manner, the inspection apparatus 1 can mutually complement the images in the regions of the dead angles that are formed by crossing of the arch-like lighting unit 31 with the images captured by the first camera 51 and the images captured by the second camera 52 among the images of the light reflection surface 101 of the inspection target 100 that have been continuously captured by the imaging devices 5 while scanning the light reflection surface 101 with the inspection light from the arch-like lighting unit 31 along the scanning direction Y. As a result, the inspection apparatus 1 can emit the inspection light to the entire surface of the light reflection surface 101 with the one-time relative rotation of the inspection target 100 and the arch-like lighting unit 31 for inspection, thereby reducing an inspection period of time and improving the inspection efficiency while preventing the apparatus from being increased in size.

The above-mentioned inspection apparatus according to the embodiment of the present invention is not limited to the above-mentioned embodiment and various changes can be made in a range described in the scope of the invention.

Although the inspection apparatus 1 described above inspects the gloss abnormality of the light reflection surface 101 of the inspection target 100, the inspection apparatus 1 is not limited thereto as long as it performs inspection using the images captured with the inspection light emitted to the inspection target 100 from the arch-like lighting unit 31.

Although the inspection target 100 described above is the resin molded product in which at least the end portions of the light reflection surface 101 are formed into the curved surfaces and that has light transmittance, and, as an example, is the room lamp cover that is provided in the cabin of the vehicle, the inspection target 100 is not limited thereto and may be formed to have flat surfaces overall. In this case, the arch-like lighting unit 31 described above may not be arranged such that the top portion 31a and the end portions 31b have the above-mentioned predetermined positional relation.

Although the holding surface 21 described above is formed as the horizontal surface and configures the placement surface holding the inspection target 100 by placing the inspection target 100 thereon in the vertical direction (height direction Z), the holding surface 21 is not limited thereto and may have the configuration of holding the inspection target 100 with a holding craw, a holding arm, and the like. In this case, although the height direction Z described above is typically the vertical direction and the rotating axis direction X and the scanning direction Y are the horizontal direction, the directions are not limited thereto and the height direction Z may be, for example, the direction along the horizontal direction.

Although the rotation driving device 4 described above rotates the arch-like lighting unit 31 relatively to the inspection target 100, the rotation driving device 4 may have the configuration of rotating the inspection target 100 relatively to the arch-like lighting unit 31, alternatively. Although the inspection apparatus 1 described above includes the rotation driving device 4, the inspection apparatus 1 may not include the rotation driving device 4. In this case, the inspection apparatus 1 may have the configuration in which a plurality of the arch-like lighting units 31 are aligned along the direction corresponding to the scanning direction Y.

Although the imaging device 5 described above is provided one each on the sides of the rotating axial line C in the scanning direction Y, the number thereof is not limited thereto and only one imaging device 5 or three or more imaging devices 5 may be provided.

An inspection apparatus according to the embodiment can emit light to the light reflection surface of the inspection target, capture the image of the light reflection surface of the inspection target by which the light is reflected, and inspect the light reflection surface of the inspection target on the basis of the captured image by using the illumination device, the imaging device, and the determination device. In this case, the inspection apparatus has the configuration in which the arch-shaped lighting unit emitting the light to the light reflection surface of the inspection target is provided around the inspection target in the circular arc form and emits the light toward the inspection target, thereby providing an effect of preventing the apparatus from being increased in size.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An inspection apparatus comprising:
   a holding surface configured to hold an inspection target;
   an illumination device including an arch-like lighting unit that is provided around the inspection target held by the holding surface, in a circular arc form, and that emits light toward the inspection target;
   an imaging device configured to capture an image of a light reflection surface of the inspection target by which the light emitted from the arch-like lighting unit is reflected;
   a determination device configured to inspect the light reflection surface of the inspection target on the basis of the image captured by the imaging device; and
   a rotation driving device that relatively rotates the inspection target and the arch-like lighting unit about a rotating axial line along the holding surface.

2. The inspection apparatus according to claim 1, wherein the determination device inspects the light reflection surface of the inspection target on the basis of the image captured by the imaging device while relatively rotating the inspection target and the arch-like lighting unit by the rotation driving device.

3. The inspection apparatus according to claim 2, wherein the holding surface is configured to hold the inspection target in a height direction, at least end portions of the light reflection surface of the inspection target are formed into curved surfaces, both end portions of the arch-like lighting unit are located on an opposite side to the inspection target with respect to the holding surface in the height direction, and the rotation driving device rotates the arch-like lighting unit from a start position at which a top portion of the circular arc form of the arch-like lighting unit is located on an opposite side to the inspection target with respect to the holding surface in the height direction to an end position at which the top portion is located on an opposite side to the inspection target with respect to the holding surface, the end position being on an opposite side to the start position in a direction of scanning of the inspection target with the light by the arch-like lighting unit with the relative rotation of the inspection target and the arch-like lighting unit.

4. The inspection apparatus according to claim 2, wherein at least one imaging device is provided on both sides of the rotating axial line in a direction of scanning of the inspection target with the light by the arch-like lighting unit with the relative rotation of the inspection target and the arch-like lighting unit, and each imaging device is located on an opposite side to the inspection target with respect to the arch-like lighting unit and a position of each imaging device relative to the inspection target is fixed.

5. The inspection apparatus according to claim 3, wherein at least one imaging device is provided on both sides of the rotating axial line in a direction of scanning of the inspection target with the light by the arch-like lighting unit with the relative rotation of the inspection target and the arch-like lighting unit, and each imaging device is located on an opposite side to the inspection target with respect to the arch-like lighting unit and a position of each imaging device relative to the inspection target is fixed.

6. The inspection apparatus according to claim 2, wherein the imaging device captures an image of the light reflection surface of the inspection target a plurality of number of times with the relative rotation of the inspection target and the arch-like lighting unit, and the determination device inspects gloss abnormality of the light reflection surface of the inspection target on the basis of the images captured by the imaging device with the relative rotation of the inspection target and the arch-like lighting unit.

7. The inspection apparatus according to claim 3, wherein the imaging device captures an image of the light reflection surface of the inspection target a plurality of number of times with the relative rotation of the inspection target and the arch-like lighting unit, and the determination device inspects gloss abnormality of the light reflection surface of the inspection target on the basis of the images captured by the imaging device with the relative rotation of the inspection target and the arch-like lighting unit.

8. The inspection apparatus according to claim 4, wherein the imaging device captures an image of the light reflection surface of the inspection target a plurality of number of times with the relative rotation of the inspection target and the arch-like lighting unit, and the determination device inspects gloss abnormality of the light reflection surface of the inspection target on the basis of the images captured by the imaging device with the relative rotation of the inspection target and the arch-like lighting unit.

9. The inspection apparatus according to claim 5, wherein the imaging device captures an image of the light reflection surface of the inspection target a plurality of number of times with the relative rotation of the inspection target and the arch-like lighting unit, and the determination device inspects gloss abnormality of the light reflection surface of the inspection target on the basis of the images captured by the imaging device with the relative rotation of the inspection target and the arch-like lighting unit.

\* \* \* \* \*